United States Patent [19]

Okada et al.

[11] Patent Number: 5,807,880
[45] Date of Patent: Sep. 15, 1998

[54] AZOLE DERIVATIVE AND PHARMACEUTICAL COMPOSITION THEREOF

[75] Inventors: Minoru Okada; Toru Yoden; Eiji Kawaminami; Yoshiaki Shimada; Tsukasa Ishihara; Masafumi Kudou, all of Ibaraki, Japan

[73] Assignee: Yamanouchi Pharmaceutical Co., Ltd., Tokyo, Japan

[21] Appl. No.: 619,629

[22] PCT Filed: Sep. 28, 1994

[86] PCT No.: PCT/JP94/01593

§ 371 Date: Mar. 26, 1996

§ 102(e) Date: Mar. 26, 1996

[87] PCT Pub. No.: WO95/09157

PCT Pub. Date: Apr. 6, 1995

[30] Foreign Application Priority Data

Sep. 30, 1993 [JP] Japan ................................. 5-244944

[51] Int. Cl.⁶ ...................... A61K 31/415; C07D 403/06
[52] U.S. Cl. ........................................ 514/397; 548/312.1
[58] Field of Search .......................... 548/312.1; 514/397

[56] References Cited

FOREIGN PATENT DOCUMENTS

| 0260744 | 9/1987 | European Pat. Off. . |
|---|---|---|
| 9427989 | 5/1994 | European Pat. Off. . |

*Primary Examiner*—Patricia L. Morris
*Attorney, Agent, or Firm*—Burgess, Ryan & Wayne

[57] ABSTRACT

An azole derivative represented by the following general formula (I)

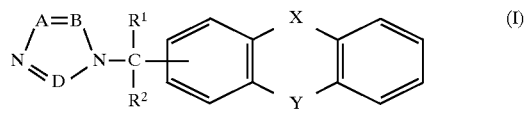

(symbols in the formula have the following meanings;

$R^1$ and $R^2$: the same or different from each other and each represents a hydrogen atom, a lower alkyl group or a phenyl group which may be substituted with a halogen atom, A, B and D: the same or different from one another and each represents a group represented by the formula

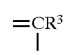

or
a nitrogen atom, X and Y: the same or different from each other and each represents a single bond, a methylene group, an oxygen atom,
a group represented by a formula $S(O)_n$, or a group represented by the formula

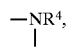

$R^3$ and $R^4$: the same or different from each other and each represents a hydrogen atom or a lower alkyl group, and
n: 0, 1 or 2),
a salt thereof, a hydrate thereof or a solvate thereof.

This compound has a function to inhibit steroid 17-20 lyase and is useful as preventive and treating agents for prostatic cancer, prostatic hypertrophy, virilism, breast cancer, mastopathy, histeromyoma, and endometriosis.

7 Claims, No Drawings

AZOLE DERIVATIVE AND PHARMACEUTICAL COMPOSITION THEREOF

TECHNICAL FIELD

This invention relates to a novel azole derivative useful as a steroid 17-20 lyase inhibitor, a pharmaceutically acceptable salt thereof and a pharmaceutical composition thereof.

BACKGROUND ART

It is known that an enzyme, called steroid 17-20 lyase, is taking a role in the formation of androgen from cholesterol in the living body at the final step of its biosynthetic pathway. Steroid 17-20 lyase uses 17α—OH pregnenolone and 17α—OH progesterone as its substrates, which have a carbon substituent at the 17β position and are formed from cholesterol, and cleaves a bonding between the 17 position carbon and the 20 position carbon of the carbon substituent, thereby effecting formation of various types of androgen. In consequence, inhibition of the enzyme activity of steroid 17-20 lyase renders possible repression of the formation of androgen and estrogen which is synthesized from androgen as its substrate and prevention and treatment of various diseases in which androgen and estrogen take parts as advancing factors. Examples of the diseases whose exacerbating factors are androgen and estrogen include prostatic cancer, prostatic hypertrophy, virilism, hypertrichosis, breast cancer, mastopathy, hysteromyoma and endometriosis.

On the other hand, it has been fully confirmed that reduction of the serum androgen level is useful in treatment of prostatic cancer and the like, and orchiectomy, LH-RH agonist or androgen antagonist is used in the clinical practice. However, orchiectomy is psychologically hardly acceptable, and the LH-RH agonist cannot block androgen except sex gland androgen and shows a transient flare phenomenon. With regard to the androgen antagonist, it has been known in recent years that its effects are reduced by mutation of androgen receptor. In consequence, it has been proposed to block effects of androgen on its receptor (total androgen block), and attempts have been made to use LH-RH agonist and androgen antagonist in combination.

A compound which inhibits steroid 17-20 lyase is considered to be a drug that can perform total androgen block by strongly blocking androgen due to its function and therefore is expected as a promising drug for the treatment of prostatic cancer and the like. In addition, being capable of reducing estrogen, a steroid 17-20 lyase inhibitor is expected as a more effective therapeutic agent for prostatic hypertrophy and as a drug having more smaller side effects in comparison with a therapeutic agent which blocks only androgen.

As steroid 17-20 lyase inhibitors, steroid type and non-steroid type compounds have been synthesized. As an example of the non-steroid type steroid 17-20 lyase inhibitor, a (1H-imidazol-1-yl)methyl-substituted imidazole derivative disclosed in an unexamined published Japanese patent application (Kokai) No. 64-85975 is known, which is a compound in which a substituted benzimidazolyl group as a condensed bicyclic group and a imidazolyl group are linked by a methine carbon or a methylene carbon.

However, the compound of the present invention has a condensed tricyclic group and therefore is structurally different from the above compound and is also a novel compound from the viewpoint of pharmacological effects because of its excellent steroid 17-20 lyase inhibiting activity and testosterone synthesis inhibiting activity as will be described later.

On the other hand, compounds having an imidazolyl group and a fluorenyl group as a condensed tricyclic group have been disclosed in an unexamined published Japanese patent application (Kokai) No. 47-1471 as a compound having an antifungal action and in U.S. Pat. No. 4,757,082 as a compound having an aromatase inhibiting function.

However, the structure of the compound of the present invention is different from those of the above compounds from a viewpoint that an azole ring is linked to a condensed benzene ring of the condensed tricyclic group via one carbon atom.

In addition, nothing is disclosed about steroid 17-20 lyase inhibiting activity of these known compounds.

As described above, various studies have been made, but development of an excellent steroid 17-20 lyase inhibitor is still an important subject in the field of medical treatment.

DISCLOSURE OF THE INVENTION

Under such a technical situation, the inventors of the present invention have conducted extensive studies on a compound which is possessed of a steroid 17-20 lyase inhibiting activity, and the present invention has been accomplished based on a finding that an azole derivative represented by the following general formula (I) or a pharmaceutically acceptable salt thereof shows excellent steroid 17-20 lyase inhibiting activity.

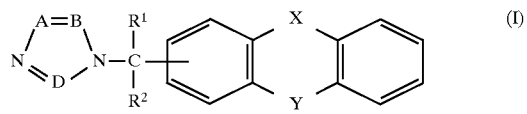

(Symbols in the formula have the following meanings;

$R^1$ and $R^2$: the same or different from each other and each represents a hydrogen atom, a lower alkyl group or a phenyl group which may be substituted with a halogen atom, A, B and D: the same or different from one another and each represents a group represented by the formula

or a nitrogen atom,

X and Y: the same or different from each other and each represents a single bond, a methylene group, an oxygen atom, a group represented by the formula $S(O)_n$, or a group represented by the formula

$R^3$ and $R^4$: the same or different from each other and each represents a hydrogen atom or a lower alkyl group, and n: 0, 1 or 2.)

Of the compounds of the present invention, preferred one is an azole derivative or a salt thereof in which, in the aforementioned general formula (I), $R^1$ and $R^2$ are the same or different from each other and each represents hydrogen atom or a lower alkyl group, X is a single bond or a group represented by the formula $S(O)_n$, and Y is methylene group, a group represented by the formula S(O)$_n$, or a group represented by the formula

more preferred one is an azole derivative or a salt thereof in which X is a single bond and Y is methylene group; and most preferred one is an azole derivative of 1-[1-(9H-fluoren-2-yl) ethyl]-1H-imidazole or a salt thereof.

The pharmaceutical composition containing the compound of the present invention, which is another object of the present invention, provides a steroid 17-20 lyase inhibitor which contains the azole derivative represented by the aforementioned general formula (I) or a pharmaceutically acceptable salt thereof as an active ingredient, particularly a steroid 17-20 lyase inhibitor which is a preventive/treating agent for prostatic cancer, prostatic hypertrophy, virilism, hypertrichosis, breast cancer, mastopathy, hysteromyoma and endometriosis, is provided.

A preferred example of the pharmaceutical composition is a steroid 17-20 lyase inhibitor which contains 1-[1-(9H-fluoren-2-yl) ethyl]-1H-imidazole or a pharmaceutically acceptable salt thereof as an active ingredient.

The compound of the present invention has a chemical structural feature in which a nitrogen atom of the azole ring is linked, via one carbon atom, to a carbon atom of the condensed tricyclic group containing X and Y and also has a pharmacological feature in that it has markedly high inhibiting activity in comparison with the imidazolylmethylimidazole derivative disclosed in an unexamined published Japanese patent application (Kokai) No. 64-85975 as a known steroid 17-20 lyase inhibitor.

The following describes the compound of the present invention in detail.

Unless otherwise noted, the term "lower" as used herein means a carbon chain having 1 to 6 carbon atoms.

According to the present invention, lower alkyl group means a straight or branched alkyl group having 1 to 6 carbon atoms. In consequence, illustrative examples of the lower alkyl group include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and the like. Of these groups, alkyl groups having 1 to 4 carbon atoms such as methyl, ethyl, propyl, isopropyl, butyl and the like are preferred, methyl and ethyl groups are more preferable, and a methyl group is further more preferable.

The "phenyl group which may be substituted with a halogen atom" may have a halogen atom at any optional position of phenyl group, and illustrative examples of the halogen atom include fluorine, chlorine, bromine and iodine or an optional combination thereof. The number of halogen atoms may be preferably 1 to 3. In consequence, examples of the "phenyl group which may be substituted with a halogen atom" include fluorophenyl, chlorophenyl, bromophenyl, iodophenyl, difluorophenyl, dichlorophenyl, dibromophenyl, bromochlorophenyl, trichlorophenyl, bromodichlorophenyl, dibromochlorophenyl, trichlorophenyl, bromodichlorophenyl, dibromochlorophenyl, bromochlorofluonyl and the like, of which a chlorophenyl group is preferred, and a 3-chlorophenyl group is more preferable.

Illustrative examples of the group represented by the formula

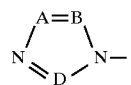

include imidazolyl, 1H-1,2,3-triazolyl, 1H-1,2,4-triazolyl, 4H-1,2,4-triazolyl, 1H-1,2,3,4-tetrazolyl, 3H-1,2,3,4-tetrazolyl and the like, of which imidazolyl, 1H-1,2,4-triazolyl and 4H-1,2,4-triazolyl groups are preferred, and an imidazolyl group is more preferable.

Illustrative examples of the group represented by the

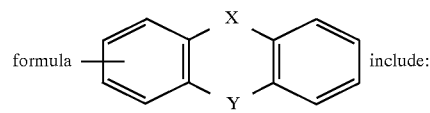

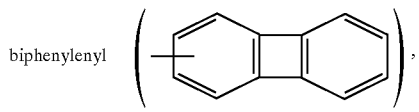

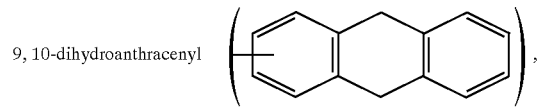

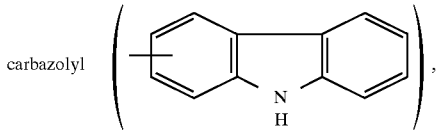

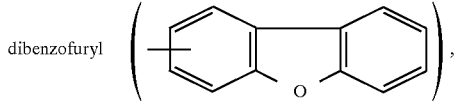

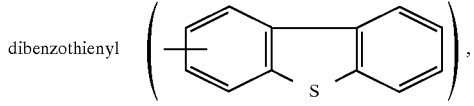

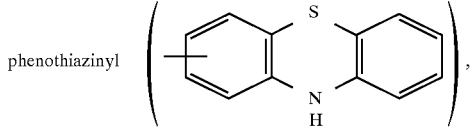

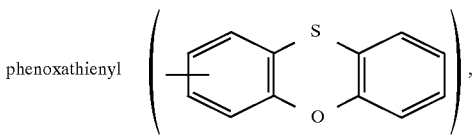

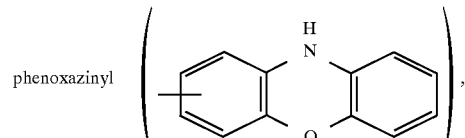

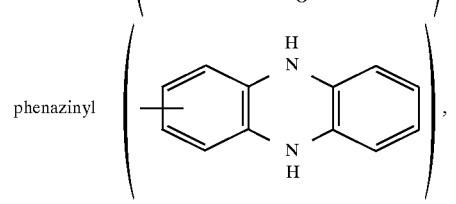

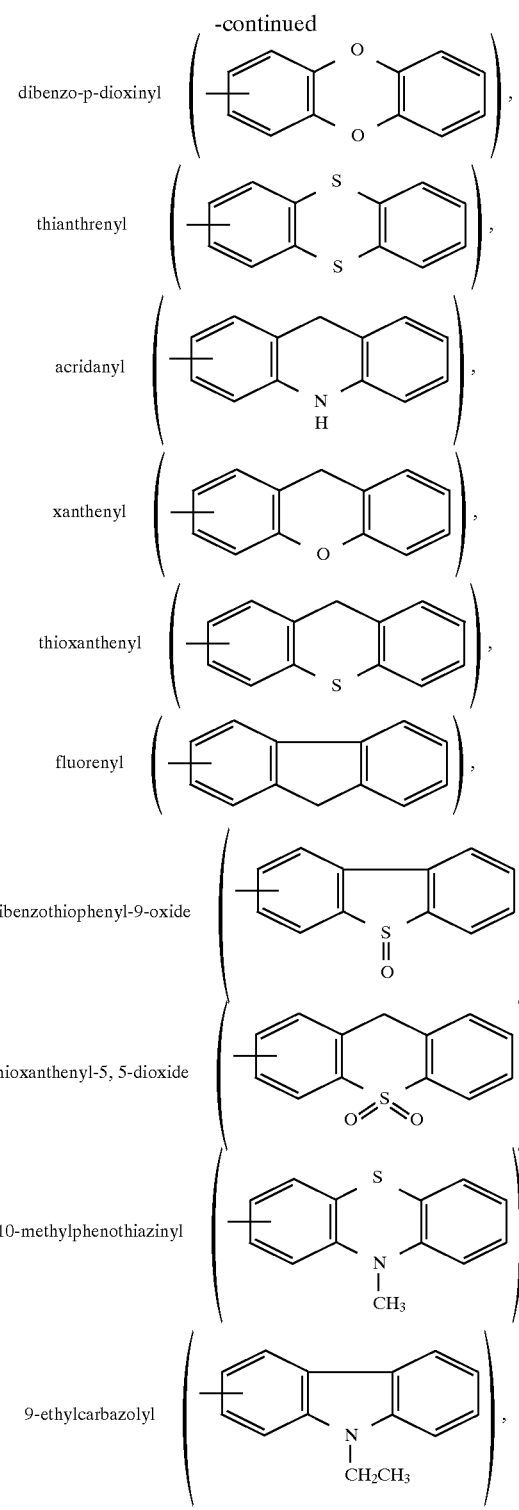

and the like, of which fluorenyl, dibenzothienyl, dibenzofuryl, dibenzothiophenyl-9-oxide, phenothiazinyl and 10-methylphenothiazinyl are preferred, and a 2-fluorenyl is more preferable.

The compound of the present invention can form salts. Pharmaceutically acceptable salts are included in the present invention. Illustrative examples of such salts include acid addition salts with inorganic acids such as hydrochloric acid, hydrobromic acid, hydroiodic acid, sulfuric acid, nitric acid, phosphoric acid and the like and with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid and the like.

Depending on the kinds of substituents, it can also form salts with alkali or alkaline earth metals (e.g., sodium, potassium, magnesium or calcium), ammonia, or organic amines (e.g., triethylamine).

Depending on the kinds of substituents, the compound of the present invention may have an asymmetric carbon atom, and such a compound forms optical isomers based on the asymmetric carbon atom, or diastereomers when it has two or more asymmetric carbon atoms. Each of these isomers alone in the isolated form and mixtures thereof are all included in the present invention.

In some cases, it may also form various types of hydrates and solvates or have polymorphism, and such compounds in isolated forms or mixtures are also included in the present invention.

The compound of the present invention and salts thereof can be produced by employing various synthetic techniques making use of the characteristics of its basic structure and kinds of its substituents.

Typical examples of the production method of the compound of the present invention are described in the following.

First Production Method

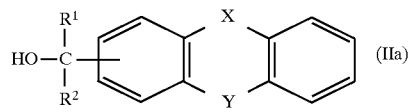

Step 1 ↓

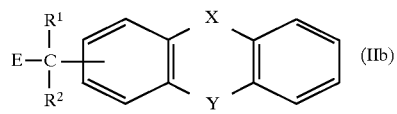

Step 2 ↓ $\begin{matrix} A=B \\ N \diagdown \\ \phantom{N} \diagup NH \\ N=D \end{matrix}$ (III)

↓

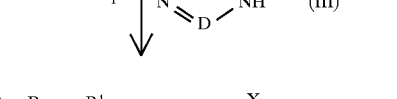

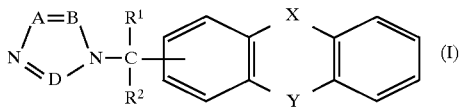

(In the above formulae, E represents a leaving group such as a halogen atom, a sulfonyloxy group or the like, and A, B, D, X, Y, $R^1$ and $R^2$ are as defined in the foregoing.)

Examples of the sulfonyloxy group includes methylsulfonyloxy, ethanesulfonyloxy, p-toluenesulfonyloxy and the like.

For example, the alkyl derivative (IIa) as a secondary or tertiary alcohol is activated by halogenation or sulfonic acid esterification in the first step, and the activated derivative is allowed to react with the azole (III) in the second step to obtain the azole derivative (I) of the present invention. In this case, the second step reaction may be carried out without isolating the product of the first step.

In the first step, halogenation can be effected by allowing the alcohol to react with the equivalent or excess molar ratio of thionyl chloride, phosphorus pentachloride, oxalyl chloride or the like. Alternatively, sulfonic acid esterification may be effected by allowing the alcohol to react with p-toluenesulfonyl chloride, methylsulfonyl chloride or the like.

The reaction of the first step is carried out at a temperature of from 0° C. to reflux temperature of a solvent inert to the reaction such as halogenated hydrocarbons (e.g., methylene chloride, chloroform, and 1,2-dichloroethane) and aromatic hydrocarbons (e.g., benzene and toluene).

In the second step, the azole (III) such as imidazole, triazole or the like acts as a base, so that it is not necessary to use other bases. In this case, the azole (III) is used in 2 to 10 times the amount of the alkyl derivative (IIb) and the reaction is carried out at 50° to 150° C. In that case, the azole itself can be used as a solvent, and an organic solvent inert to the reaction, such as dimethylformamide, dimethyl sulfoxide, tetrahydrofuran, toluene, acetonitrile or the like may further coexist.

Alternatively, the second step reaction may be carried out at 0° to 100° C. by adding a base and using the alkyl derivative (IIb) and equivalent or excess amount of the azole (III) such as imidazole, triazole or the like. Examples of the base include sodium hydride, potassium hydride, potassium bistrimethylsilylamide, sodium amide, n-butyl lithium, potassium t-butoxide, sodium, sodium methoxide, sodium ethoxide and the like. When a base is used, the reaction is carried out in an organic solvent inert to the reaction such as dimethylformamide, dimethyl sulfoxide, tetrahydrofuran, toluene, acetonitrile or the like.

Second Production Method

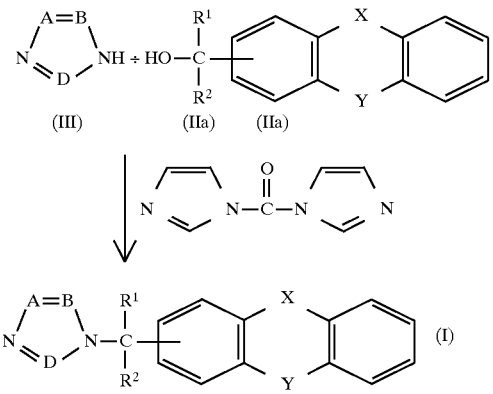

(In the above formulae, A, B, D, X, Y, $R^1$ and $R^2$ are as defined in the foregoing.)

The compound (I) of the present invention can also be produced by carrying out dehydration reaction of the azole compound (III) with the compound (IIa) using a dehydrating condensing agent such as 1,1'-carbonyldiimidazole or the like.

The reaction is carried out at the temperature of from ice-cooling temperature to heating under reflux using a solvent such as dichloromethane, chloroform, dichloroethane, and tetrahydrofuran.

In these production methods, the synthesis can also be carried out using a protecting group when X and Y are NH and the like.

Examples of the protecting group include dimethylsulfonyl, benzenesulfonyl, p-toluenesulfonyl, acetyl, Boc and the like. Elimination of the protecting group can be effected by a known method conventionally used.

The thus produced compound of the present invention is isolated and purified as a free compound or its salt, hydrate, solvate or the like. Pharmaceutically acceptable salts of the compound (I) of the present invention can also be produced by subjecting it to conventional salt forming reactions.

Isolation and purification are carried out by applying usual chemical procedures such as extraction, fractional crystallization, various types of fractional chromatography and the like.

In addition, optical isomers can be made into stereochemically pure isomers by selecting appropriate starting compounds or by carrying out racemic resolution of racemic compound (for example, a method in which a compound is made into a diastereomer salt with a generally used optically active base and then subjected to optical resolution).

INDUSTRIAL APPLICABILITY

The compound of the present invention is possessed of a function to inhibit activity of steroid 17-20 lyase which is an enzyme that takes a role in the formation of androgen from cholesterol in the living body. In consequence, the compound of the present invention is useful as preventive and treating drugs for various diseases whose exacerbating factors are androgen and estrogen which is synthesized from androgen as its substrate, such as prostatic cancer, prostatic hypertrophy, virilism, hypertrichosis, breast cancer, mastopathy, hysteromyoma and endometriosis.

Utility of the compound of the present invention has been confirmed by the following tests.

(1) Measurement of rat steroid 17-20 lyase inhibiting activity

Carried out in accordance with the procedure described in J. Steroid Biochem., Vol.33, No.6, 1191–1195 (1989).

A testis was excised from a ten-week-old male Wistar rat, homogenized and then centrifuged to obtain microsomes. A 50 μg portion of the microsomal protein, 1 μM of $[1,2-^3H]$-17α-hydroxyprogesterone ($5.55 \times 10^5$ dpm) and a test compound were dissolved in 100 μl of 50 mM phosphate buffer (pH 7.4), and the solution was mixed with NADPH solution and incubated at 37° C. for 60 minutes. This was mixed with 400 μl of a mixed solvent of methanol and tetrahydrofuran (2:3) and subjected to centrifugation, and radioactivities of the substrate and products (androstenedione and testosterone) in the resulting supernatant fluid were measured using a high performance liquid chromatography (HPLC) equipped with a radioactive isotope detector to examine activity of the test compound to inhibit steroid 17-20 lyase.

(2) Measurement of in vivo rat testosterone synthesis inhibiting activity

Carried out in accordance with the procedure described in J. Steroid Biochem., Vol.32, No.6, 781–788 (1989).

Each test drug was orally administered to ten-week-old male Wistar rats under fasting. One hour after the drug administration, LH-RH (60 ng/rat) was administered by intramuscular injection to accelerate testosterone synthesis. One hour thereafter, blood was collected by decapitation, and concentration of testosterone in the thus obtained serum was measured by a radioactive isotope assay to calculate testosterone synthesis inhibiting activity.

[Test results]

Results of the tests with respect to the compound of the present invention are shown in the following.

(1) Measurement of rat steroid 17-20 lyase inhibiting activity

The steroid 17-20 lyase inhibiting activity in rat testicular microsomes was calculated as $IC_{50}$ value by the method described in the above test method (1), with the results shown in Table 1.

TABLE 1

| Compound | Concentration of drug to inhibit 50% of steroid 17–20 lyase activity |
| --- | --- |
| Example 2 | $IC_{50}$ = 4.0 nM |
| Example 4 | 5.0 nM |
| Example 8 | 5.7 nM |
| Example 10 | 6.9 nM |
| Control compound | 420 nM |

(Note) The control compound is that disclosed as a compound of Example 187 in an unexamined published Japanese patent application (Kokai) No. 64-85975.

The control compound was measured by the same method, but the compound of the present invention showed 60 times or more higher activity.

(2) Measurement of in vivo rat testosterone synthesis inhibiting activity

The in vivo activity to inhibit synthesis of testosterone in rats measured by the above test method (2) was expressed as a testosterone synthesis inhibition ratio (%) to the control group when each test compound or a control compound was administered in a dose of 1 or 10 mg/kg (Table 2).

TABLE 2

| Compound | Dose | Testosterone synthesis inhibition ratio |
| --- | --- | --- |
| Example 2 | 1 mg/kg | 86.3% |
| Example 7 | " | 78.4% |
| Example 8 | " | 73.0% |
| Control compound | 10 mg/kg | 47.0% |

(Note) The control compound is that disclosed as a compound of Example 187 in an unexamined published Japanese patent application (Kokai) No. 64-85975.

The compound of the present invention showed markedly superior inhibiting effect also with regard to the rat testosterone synthesis inhibiting activity at a 1/10 dose of the control compound.

A pharmaceutical composition which contains at least one of the compounds represented by the general formula (I) and pharmaceutically acceptable salts, hydrates or the like thereof as the active ingredient is prepared using carriers, excipients and other additives commonly used for the preparation of medicines and administered either by oral administration or parenteral administration in the dosage form of tablets, powders, fine granules, granules, capsules, pills, solutions, injections, suppositories and the like.

Though the dose is optionally decided in individual cases, taking symptoms of the disease and age, sex, weight and the like of each patient into consideration, it may be orally administered in the range of generally from 0.1 to 100 mg, preferably from 0.1 to 10 mg, per day per adult once a day or dividing the daily dose into several doses per day, or administered by parenteral administration within the range of from 0.1 to 100 mg per day per adult once a day or dividing the daily dose into several doses per day or by intravenous continuous injection within the range of from 1 to 24 hours per day. As a matter of course, since the daily dose varies depending on various conditions as described above, a dose smaller than the above range may be effective in some cases.

The solid composition of the present invention for oral administration use may be used in the dosage form of tablets, powders, granules and the like. In such a solid composition, at least one active ingredient is mixed with at least one inert diluent such as lactose, mannitol, glucose, hydroxypropylcellulose, fine crystalline cellulose, starch, polyvinylpyrrolidone, magnesium metasilicate aluminate or the like. In the usual way, the composition may contain additives other than the inert diluent, such as lubricants (e.g., magnesium stearate), disintegrators (e.g., calcium caroxymethylcellulose), stabilizers (e.g., lactose) and solubilizers (e.g., glutamic acid, aspartic acid). As occasion demands, tablets or pills may be coated with a gastric or enteric film such as of sucrose, gelatin, hydroxypropylcellulose, hydroxypropylmethylcellulose phthalate or the like.

The liquid composition for use in oral administration includes pharmaceutically acceptable emulsions, solutions, suspensions, syrups, elixirs and the like and contains generally used inert diluents such as purified water, ethanol and the like. In addition to the inert diluent, this composition may also contain auxiliary agents such as a solubilizing agent or a solution aid, a moistening agent, a suspending agent and the like, and sweeteners, flavors, aromatic agents, antiseptics and the like.

Injections for use in parenteral administration include aseptic aqueous or non-aqueous solutions, suspensions and emulsions. Examples of the diluent of the aqueous solutions and suspensions include distilled water and physiological saline for injection use. Examples of the diluent of non-aqueous solutions and suspensions include propylene glycol, polyethylene glycol, plant oils such as olive oil and the like, alcohols such as ethanol and the like and Polysorbate 80 (trade name). Such compositions may further contain auxiliary agents such as tonicity agents, antiseptics, moistening agents, emulsifying agents, dispersing agents, stabilizing agents (e.g., lactose), solubilizing agents or solution aids and the like. These compositions are sterilized by bacterial filtration, blending of bactericides or irradiation. Alternatively, a sterile solid composition prepared in advance may be used by dissolving it in sterile water or a sterile solvent for injection use prior to its use.

BEST MODE OF CARRYING OUT THE INVENTION

The present invention will be further illustrated by way of Examples, but the present invention should not be construed as being limited thereto.

EXAMPLE 1

(1) Thionyl chloride (1.1 ml) and catalytically effective amount of N,N-dimethylformamide were added to a solution of 2-(1-hydroxyethyl)-9H-fluorene (1.05 g) in methylene chloride (15 ml) under ice-cooling, and the mixture was stirred at room temperature for 30 minutes and then heated under reflux for 1 hour. By evaporating the solvent under reduced pressure, 2-(1-chloroethyl)-9H-fluorene was obtained.

(2) The thus obtained 2-(1-chloroethyl)-9H-fluorene was dissolved in 20 ml of N,N-dimethylformamide, and the solution was mixed with imidazole (2.72 g), followed by stirring at 100° C. for 2 hours. The solvent was evaporated under a reduced pressure, and water was added to the resulting residue, followed by extraction with chloroform. The chloroform layer was washed with water and dried over anhydrous magnesium sulfate, the solvent was evaporated under a reduced pressure and then the resulting residue was purified by silica gel column chromatography to obtain crude crystals from the eluate of a mixed solvent of chloroform and methanol (200:1). By recrystallizing the crude crystals from a mixed solvent of ethyl acetate and ether, 0.6 g of 1-[1-(9H-fluoren-2-yl) ethyl]-1H-imidazole was obtained.

Elemental analysis (for $C_{18}H_{16}N_2$)

|  | C (%) | H (%) | N (%) |
|---|---|---|---|
| calcd. | 83.04 | 6.19 | 10.76 |
| found | 83.14 | 6.16 | 10.80 |

Nuclear magnetic resonance spectrum ($CDCl_3$, TMS internal standard):

δ: 1.91 (3H, d, J=7 Hz), 3.86 (2H, s), 5.42; (1H, q, J=7 Hz), 6.97 (1H, s), 7.10 (1H, s), 7.19; (1H, d, J=8 Hz), 7.29–7.33 (2H, m), 7.38; (1H, t, J=7 Hz), 7.54 (1H, d, J=7 Hz), 7.63 (1H, s), 7.73–7.78 (2H, m)

EXAMPLE 2

1-[1-(9H-Fluoren-2-yl)ethyl]-1H-imidazole (8.88 g) was dissolved in ethyl acetate, and 15 ml of 4N hydrogen chloride-ethyl acetate was added to this solution under ice-cooling. The thus precipitated crystals were collected by filtration and washed with ethyl acetate to obtain 9.95 g of 1-[1-(9H-fluoren-2-yl)ethyl]-1H-imidazole hydrochloride.

Elemental analysis (for $C_{18}H_{17}N_2Cl$)

|  | C (%) | H (%) | N (%) | Cl (%) |
|---|---|---|---|---|
| calcd. | 72.84 | 5.77 | 9.44 | 11.95 |
| found | 72.57 | 5.72 | 9.40 | 11.79 |

Nuclear magnetic resonance spectrum (DMSO-$d_6$, TMS internal standard):

δ: 1.96 (3H, d, J=7 Hz), 3.94 (2H, s), 5.92; (1H, q, J=7 Hz), 7.32–7.41 (2H, m), 7.49; (1H, d, J=8 Hz), 7.60 (1H, d, J=8 Hz), 7.69 (1H, s), 7.73 (1H, s), 7.91–7.95 (3H, m), 9.48 (1H, s)

EXAMPLE 3

Using α-(9H-fluoren-2-yl)-3-chlorobenzyl alcohol and imidazole as starting compounds, the process of Example 1 was repeated to obtain 1-[3-chloro-α-(9H-fluoren-2-yl)benzyl]-1H-imidazole.

Elemental analysis (for $C_{23}H_{17}N_2Cl$)

|  | C (%) | H (%) | N (%) | Cl (%) |
|---|---|---|---|---|
| calcd. | 77.41 | 4.80 | 7.85 | 9.93 |
| found | 77.53 | 4.80 | 7.76 | 10.05 |

Nuclear magnetic resonance spectrum ($CDCl_3$, TMS internal standard):

δ: 3.87 (2H, s), 6.56 (1H, s), 6.88 (1H, s), 7.01; (1H, d, J=7 Hz), 7.13 (2H, d, J=6 Hz), 7.28–7.40; (4H, m), 7.46 (1H, s), 7.54 (1H, d, J=7 Hz), 7.75–7.79; (2H, m), 7.14 (1H, s), 7.26 (1H, s)

EXAMPLE 4

Using 2-(9H-fluoren-2-yl)propanol and imidazole as starting compounds, the process of Example 1 was repeated to obtain 1-[1-(9H-fluoren-2-yl)-1-methylethyl]-1H-imidazole.

Elemental analysis (for $C_{19}H_{18}N_2$)

|  | C (%) | H (%) | N (%) |
|---|---|---|---|
| calcd. | 83.18 | 6.61 | 10.21 |
| found | 83.21 | 6.80 | 10.21 |

Nuclear magnetic resonance spectrum ($CDCl_3$, TMS internal standard):

δ: 1.97 (6H, s), 3.85 (2H, s), 6.95 (1H, s), 7.12–7.3 (2H, m), 7.21 (1H, s), 7.30 (1H, t, J=7 Hz), 7.37 (1H, t, J=7 Hz), 7.53 (1H, d, J=8 Hz), 7.68–7.72 (2H, m), 7.76 (1H, d, J=7 Hz)

EXAMPLES 5 AND 6

(1) Thionyl chloride (0.83 ml) and catalytically effective amount of N,N-dimethylformamide were added to a solution of 2-(1-hydroxy)ethyl-9H-fluorene (0.8 g) in methylene chloride (10 ml) under ice-cooling, and the mixture was stirred at room temperature for 30 minutes and then heated under reflux for 1 hour. By evaporating the solvent to dryness under a reduced pressure, 2-(1-chloroethyl)-9H-fluorene was obtained.

(2) The thus obtained 2-(1-chloroethyl)-9H-fluorene was mixed with 1,2,4-triazole (1.31 g) and heated at 120° C. for 30 minutes without further adding solvent. After cooling, water was added to the reaction mixture, followed by extraction with ethyl acetate. The organic layer was dried over anhydrous magnesium sulfate, the solvent was evaporated and then the resulting residue was subjected to silica gel column chromatography. First, elution was carried out with a mixed solvent of chloroform and methanol (50:1), and the thus obtained crude crystals were recrystallized from a mixed solvent of ether and ethyl acetate to obtain 0.24 g of 1-[1-(9H-fluoren-2-yl) ethyl]-1H-1,2,4-triazole (Example 5). Thereafter, crude crystals obtained from the chloroform-methanol (50:1) eluate were recrystallized from a mixed solvent of ethyl acetate and ether to obtain 0.25 g of 4-[1-(9H-fluoren-2-yl) ethyl]-4H-1,2,4-triazole (Example 6).

EXAMPLE 5

Elemental analysis (for $C_{17}H_{15}N_3$)

|  | C (%) | H (%) | N (%) |
|---|---|---|---|
| calcd. | 78.13 | 5.79 | 16.08 |
| found | 78.32 | 5.80 | 16.12 |

Nuclear magnetic resonance spectrum ($CDCl_3$, TMS internal standard):

δ: 1.99 (3H, d, J=7 Hz), 3.88 (2H, s), 5.63 (1H, q, J=7 Hz), 7.28–7.33 (2H, m), 7.38 (1H, t, J=7 Hz), 7.44 (1H, s), 7.54 (1H, d, J=7 Hz), 7.76–7.78 (2H, m), 7.99 (1H, s), 8.08 (1H, s)

EXAMPLE 6

Elemental analysis (for $C_{17}H_{15}N_3$)

|  | C (%) | H (%) | N (%) |
|---|---|---|---|
| calcd. | 78.13 | 5.79 | 16.08 |
| found | 78.29 | 5.75 | 16.25 |

Nuclear magnetic resonance spectrum (CDCl$_3$, TMS internal standard):

δ: 1.96 (3H, d, J=7 Hz), 3.88 (2H, s), 5.48 (1H, q, J=7 Hz), 7.22 (1H, d, J=8 Hz), 7.32–7.35 (2H, m), 7.33 (1H, s), 7.39 (1H, t, J=7 Hz), 7.55 (1H, d, J=8 Hz), 7.77–7.79 (2H, m), 8.22 (2H, s)

The following compounds of Examples 7 to 13 were obtained by a method similar to that of Example 1.

EXAMPLE 7

1-[(9H-Fluoren-2-yl)methyl]-1H-imidazole
Starting compounds: 2-hydroxymethyl-9H-fluorene and imidazole
Physicochemical properties
Melting point: 193°–194° C. Nuclear magnetic resonance spectrum (CDCl$_3$, TMS internal standard):

δ: 3.86 (2H, s), 5.17 (2H, s), 6.94 (1H, s), 7.11 (1H, s), 7.19 (1H, d, J=8 Hz), 7.29–7.33 (2H, m), 7.38 (1H, t, J=7 Hz), 7.54 (1H, d, J=7 Hz), 7.58 (1H, s), 7.74–7.78 (2H, m)

EXAMPLE 8

1-[1-(Dibenzothiophen-3-yl)ethyl]-1H-imidazole
Starting compounds: 3-(1-hydroxyethyl)dibenzothiophene and imidazole
Physicochemical properties
Melting point: 103°–105° C.; Nuclear magnetic resonance spectrum (CDCl$_3$, TMS internal standard):

δ: 1.96 (3H, d, J=7 Hz), 5.51 (1H, q, J=7 Hz), 6.98 (1H, s), 7.12 (1H, s), 7.24 (1H, dd, J=8 Hz, 2 Hz), 7.46–7.48 (2H, m), 7.61 (1H, s), 7.66 (1H, s), 7.84–7.86 (1H, m), 8.10–8.15 (2H, m)

EXAMPLE 9

1-[1-(Dibenzofuran-3-yl)ethyl]-1H-imidazole
Starting compounds: 2-(3-dibenzofuranyl)propanol and imidazole
Physicochemical properties
Melting point: 98°–99° C.; Nuclear magnetic resonance spectrum (CDCl$_3$, TMS internal standard):

δ: 1.95 (3H, d, J=7 Hz), 5.51 (1H, q, J=7 Hz), 6.97 (1H, s), 7.11 (1H, s), 7.14 (1H, d, J=8 Hz), 7.33–7.48 (3H, m), 7.56 (1H, d, J=8 Hz), 7.65 (1H, s), 7.90 (1H, d, J=8 Hz), 7.93 (1H, d, J=8 Hz)

EXAMPLE 10

2-[1-(1H-Imidazol-1-yl)ethyl]phenothiazine monooxalate
Starting compounds: 2-(1-hydroxyethyl)phenothiazine and imidazole
Physicochemical properties
Mass spectrometry data (m/z): 293 (M$^+$) (as free base)
Nuclear magnetic resonance spectrum (DMSO-d$_6$, TMS internal standard):

δ: 1.76 (3H, d, J=7 Hz), 5.53 (1H, q, J=7 Hz), 6.50 (1H, s), 6.60–6.75 (3H, m), 6.83–6.99 (3H, m), 7.32 (1H, s), 7.50 (1H, s), 8.51 (1H, s), 8.62 (1H, s)

EXAMPLE 11

2-[[1-(1H-Imidazol-1-yl)ethyl]-10-methyl] phenothiazine monofumarate
Starting compounds: 2-(1-hydroxyethyl)-10-methylphenothiazine and imidazole Physicochemical properties Elemental analysis (for C$_{22}$H$_{21}$N$_3$O$_4$S)

| | C (%) | H (%) | N (%) | S (%) |
|---|---|---|---|---|
| calcd. | 62.40 | 5.00 | 9.92 | 7.57 |
| found | 62.02 | 5.07 | 9.82 | 7.17 |

Nuclear magnetic resonance spectrum (DMSO-d$_6$, TMS internal standard):

δ: 1.79 (3H, d, J=7 Hz), 3.30 (3H, s), 5.50 (1H, q, J=7 Hz), 6.63 (2H, s), 6.84–6.88 (2H, m), 6.94–6.97 (3H, m), 7.11–7.15 (2H, m), 7.21 (1H, t, J=9 Hz), 7.33 (1H, s), 7.91 (1H, s)

EXAMPLE 12

1-[1-(9H-Fluoren-2-yl)butyl]-1H-imidazole
Starting compounds: 1-(9H-fluoren-2-yl)butanol and imidazole
Physicochemical properties
Melting point: 73°–74° C. Nuclear magnetic resonance spectrum (CDCl$_3$, TMS internal standard):

δ: 0.98 (3H, t, J=7 Hz), 1.31–1.38 (2H, m), 2.16–2.30 (2H, m), 3.86 (2H, s), 5.18 (1H, t, J=8 Hz), 6.98 (1H, s), 7.08 (1H, s), 7.22 (1H, d, J=8 Hz), 7.30–7.38 (3H, m), 7.53 (1H, d, J=7 Hz), 7.64 (1H, s), 7.73 (1H, d, J=8 Hz), 7.76 (1H, d, J=8 Hz)

EXAMPLE 13

1-[(9H-Fluoren-2-yl)(phenyl)methyl]-1H-imidazole
Starting compounds: α-(9H-fluoren-2-yl)benzyl alcohol and imidazole
Physicochemical properties
Melting point: 141°–142° C.; Nuclear magnetic resonance spectrum (CDCl$_3$, TMS internal standard):

δ: 3.86 (2H, s), 6.59 (1H, s), 6.89 (1H, s), 7.11–7.40 (10H, m), 7.45 (1H, s), 7.53 (1H, d, J=7 Hz), 7.76 (2H, dd, J=7 Hz, 7 Hz)

EXAMPLE 14

1H-1,2,3-Triazole (1.64 g) was added to 2-(1-chloroethyl)-9H-fluorene (1.1 g), followed by heating at 120° C. for 30 minutes. After cooling, water was added and the mixture was extracted with chloroform. The organic layer was dried over anhydrous magnesium sulfate, the solvent was evaporated and then the thus obtained residue was subjected to silica gel column chromatography. Crude crystals obtained from the chloroform eluent were recrystallized from ethyl acetate to obtain 0.62 g of 1-[1-(9H-fluoren-2-yl)ethyl]-1H-1,2,3-triazole.

Physicochemical properties
Melting point: 160°–162° C.; Nuclear magnetic resonance spectrum (CDCl$_3$, TMS internal standard):

δ: 2.05 (3H, d, J=7 Hz), 3.87 (2H, s), 5.92 (1H, q, J=7 Hz), 7.26–7.39 (3H, m), 7.44 (1H, s), 7.48 (1H, d, J=1 Hz), 7.54 (1H, d, J=8 Hz), 7.70 (1H, d, J=1 Hz), 7.74–7.78 (2H, m)

EXAMPLE 15

Under ice-cooling, m-chloroperbenzoic acid (0.18 g) was gradually added in small portions to a solution of 1-[1-(dibenzothiophen-3-yl) ethyl]-1H-imidazole (0.2 g) obtained in Example 8 in chloroform (5 ml), and the mixture was stirred at the same temperature for 2 hours. A saturated sodium bicarbonate aqueous solution was added and the chloroform layer was separated and dried over anhydrous magnesium sulfate. After evaporation of the solvent, the resulting residue was purified by silica gel column chromatography to obtain an oily material from a chloroform-methanol (100:1) eluate. This oily material was dissolved in acetone and mixed with 40 mg of fumaric acid which was dissolved by heating. After cooling, the thus precipitated crystals were washed with acetone to obtain 90 mg of 3-[1-(1H-imidazol-1-yl)ethyl]dibenzothiophene-5-oxide monofumarate.

Physicochemical properties

Mass spectrometry data (m/z): (FAB): 295 M+H)$^+$(as free base)

Nuclear magnetic resonance spectrum (DMSO-$d_6$, TMS internal standard):

δ: 1.88 (3H, d, J=7 Hz), 5.71 (1H, q, J=7 Hz), 6.63 (2H, s), 6.97 (1H, s), 7.39 (1H, s), 7.57–7.63 (2H, m), 7.71 (1H, t, J=8 Hz), 7.93 (1H, s), 8.01–8.13 (4H, m)

EXAMPLE 16

(1) Thionyl chloride (0.26 ml, 3.54 mmol) and catalytically effective amount of DMF were added at room temperature to a solution of 9-benzenesulfonyl-2-(1-hydroxyethyl)carbazole (0.621 g, 1.77 mmol) in methylene chloride, and the mixture was heated under reflux for 1.5 hours. After evaporation of the solvent under reduced pressure, the thus obtained residue was mixed with ethyl acetate and washed with saturated sodium bicarbonate aqueous solution and saturated sodium chloride aqueous solution in that order, the organic layer was dried over magnesium sulfate and then the solvent was evaporated under reduced pressure to obtain 9-benzenesulfonyl-2-(1-chloroethyl)carbazole.

(2) Imidazole (1.21 g, 17.7 mmol) was added to a solution of the thus obtained 9-benzenesulfonyl-2-(1-chloroethyl)carbazole in DMF (8 ml) at room temperature and the mixture was stirred at 120° C. for 2.5 hours. The reaction solution was partitioned between ethyl acetate and distilled water. The organic layer was washed with saturated sodium chloride aqueous solution and dried over magnesium sulfate. The solvent was evaporated under reduced pressure and the resulting residue was purified by silica gel column chromatography to obtain 0.456 g (1.14 mmol, 61%) of oily material of 9-benzenesulfonyl-2-[1-(1H-imidazol-1-yl)ethyl]carbazole from the eluate of chloroform-methanol (120:1).

Physicochemical properties

Nuclear magnetic resonance spectrum (DMSO-$d_6$, TMS internal standard):

δ: 1.91 (3H, d, J=7 Hz), 5.79 (1H, q, J=7 Hz), 7.01 (1H, s), 7.35 (1H, s), 7.39–7.74 (8H, m), 7.91 (1H, s), 8.01 (1H, p), 8.09–8.12 (2H, m), 8.27 (1H, d, J=8 Hz)

(3) A mixed solution of the thus obtained 9-benzenesulfonyl-2-[1-(1H-imidazol-1-yl)ethyl]carbazole (0.436 g, 1.09 mmol), ethanol (50 ml) and 2N sodium hydroxide aqueous solution (10 ml) was heated under reflux for 4 hours. After evaporation of volatile components under reduced pressure, the resulting residue was mixed with chloroform and washed with saturated sodium chloride aqueous solution, and the organic layer was dried over magnesium sulfate. After evaporation of the solvent under reduced pressure, the resulting residue was purified by silica gel column chromatography to obtain crude crystals from the eluate of chloroform-methanol (100:1). By recrystallizing the crude crystals from ethyl acetate, 0.174 g of 2-[1-(1H-imidazol-1-yl) ethyl]carbazole was obtained.

Physicochemical properties

Melting point: 157°–158° C.; Nuclear magnetic resonance spectrum (DMSO-$d_6$, TMS internal standard):

δ: 1.87 (3H, d, J=7 Hz), 5.69 (1H, q, J=7 Hz), 6.93 (1H, s), 7.10–7.47 (6H, m), 7.85 (1H, s), 8.06–8.09 (2H, m), 11.25 (1H, s)

Chemical structures of the compounds obtained in the above Examples are shown in the following table.

In the table, the binding position means a position where

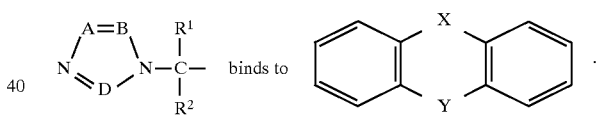

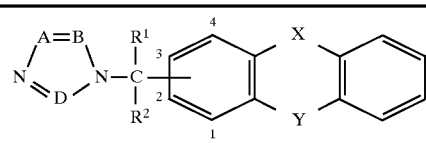

| Ex. No. | A | B | D | R$^1$ | R$^2$ | Binding Position | X | Y | Salt |
|---|---|---|---|---|---|---|---|---|---|
| 1 | CH | CH | CH | CH$_3$ | H | 2 | Bond | CH$_2$ | — |
| 2 | CH | CH | CH | CH$_3$ | H | 2 | Bond | CH$_2$ | Hydrochloride |
| 3 | CH | CH | CH | 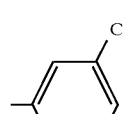 | H | 2 | Bond | CH$_2$ | — |
| 4 | CH | CH | CH | CH$_3$ | CH$_3$ | 2 | Bond | CH$_2$ | — |
| 5 | CH | N | CH | CH$_3$ | H | 2 | Bond | CH$_2$ | — |
| 6 | N | CH | CH | CH$_3$ | H | 2 | Bond | CH$_2$ | — |

-continued

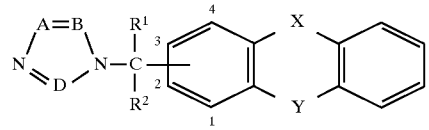

| Ex. No. | A | B | D | R¹ | R² | Binding Position | X | Y | Salt |
|---|---|---|---|---|---|---|---|---|---|
| 7 | CH | CH | CH | H | H | 2 | Bond | CH₂ | — |
| 8 | CH | CH | CH | CH₃ | H | 2 | Bond | S | — |
| 9 | CH | CH | CH | CH₃ | H | 2 | Bond | O | — |
| 10 | CH | CH | CH | CH₃ | H | 2 | S | NH | Oxalate |
| 11 | CH | CH | CH | CH₃ | H | 2 | S | N—CH₃ | Fumarate |
| 12 | CH | CH | CH | CH₂CH₂CH₃ | H | 2 | Bond | CH₂ | — |
| 13 | CH | CH | CH | phenyl | H | 2 | Bond | CH₂ | — |
| 14 | CH | CH | N | CH₃ | H | 2 | Bond | CH₂ | — |
| 15 | CH | CH | CH | CH₃ | H | 2 | Bond | S→O | Fumarate |
| 16 | CH | CH | CH | CH₃ | H | 2 | Bond | NH | — |

In addition to the compounds of the aforementioned Examples, other compounds of the present invention are shown below. Since these compounds can be synthesized in accordance with the synthetic pathways and methods described in the aforementioned production processes and Examples and their modifications known to those skilled in the art, particular experiments are not required.

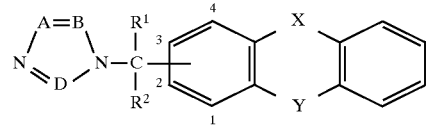

| Compound No. | A | B | D | R¹ | R² | Binding Position | X | Y |
|---|---|---|---|---|---|---|---|---|
| 1 | CH | CH | CH | CH₂CH₃ | H | 2 | Bond | CH₂ |
| 2 | CH | CH | CH | CH₂CH₂CH₃ | CH₃ | 2 | Bond | CH₂ |
| 3 | CH | CH | CH | 4-Cl-phenyl | H | 2 | Bond | CH₂ |
| 4 | CH | CH | CH | 3-Br-phenyl | CH₃ | 2 | Bond | CH₂ |
| 5 | CH | CH | CH | CH₃ | CH₃ | 2 | Bond | S |
| 6 | CH | CH | CH | CH₃ | CH₃ | 2 | S | NH |
| 7 | CH | CH | CH | CH₃ | H | 1 | Bond | CH₂ |
| 8 | CH | CH | CH | CH₃ | H | 1 | Bond | S |
| 9 | CH | CH | CH | CH₃ | H | 1 | S | NH |
| 10 | CH | CH | CH | CH₂CH₂CH₃ | H | 3 | Bond | CH₂ |
| 11 | CH | CH | CH | CH₂CH₂CH₃ | H | 3 | Bond | S |
| 12 | CH | CH | CH | CH₂CH₂CH₃ | H | 3 | S | NH |
| 13 | CH | CH | CH | CH₂CH₃ | H | 4 | Bond | CH₂ |

-continued

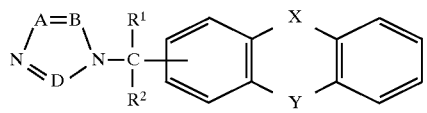

| Compound No. | A | B | D | R¹ | R² | Binding Position | X | Y |
|---|---|---|---|---|---|---|---|---|
| 14 | CH | CH | CH | Cl (2-chlorophenyl) | H | 2 | Bond | $CH_2$ |
| 15 | CH | CH | CH | $CH_3$ | H | 2 | Bond | Bond |
| 16 | CH | CH | CH | $CH_3$ | H | 2 | $CH_2$ | $CH_2$ |
| 17 | CH | CH | CH | $CH_3$ | H | 3 | S | NH |
| 18 | CH | CH | CH | $CH_3$ | H | 3 | S | O |
| 19 | CH | CH | CH | $CH_3$ | H | 2 | NH | O |
| 20 | CH | CH | CH | $CH_3$ | H | 2 | NH | NH |
| 21 | CH | CH | CH | $CH_3$ | H | 2 | O | O |
| 22 | CH | CH | CH | $CH_3$ | H | 2 | S | S |
| 23 | CH | CH | CH | $CH_3$ | H | 2 | $CH_2$ | NH |
| 24 | CH | CH | CH | $CH_3$ | H | 2 | $CH_2$ | O |
| 25 | CH | CH | CH | $CH_3$ | H | 2 | $CH_2$ | S |
| 26 | CH | CH | CH | $CH_2CH_3$ | H | 2 | Bond | NH |
| 27 | CH | CH | CH | phenyl | H | 2 | Bond | NH |
| 28 | CH | CH | CH | (chlorophenyl) | H | 2 | Bond | NH |
| 29 | CH | CH | CH | $CH_3$ | $CH_3$ | 2 | Bond | NH |
| 30 | N | CH | CH | $CH_3$ | H | 2 | Bond | NH |
| 31 | CH | N | CH | $CH_3$ | H | 2 | Bond | NH |
| 32 | CH | CH | CH | $CH_2CH_2CH_3$ | H | 2 | Bond | NH |
| 33 | CH | CH | N | $CH_3$ | H | 2 | Bond | NH |
| 34 | CH | C—$CH_3$ | CH | $CH_3$ | H | 2 | Bond | NH |

1 mg Tablet

A 7 g portion of the compound of the present invention was mixed with 534.8 g of lactose in a polyethylene bag. This mixture was pulverized using a sample mill (manufactured by Hosokawa Micron). A 541.8 g portion of the pulverized mixture was uniformly mixed with 135.1 g of corn starch in a fluidized granulation coating machine (manufactured by Ohkawara Seisakusyo). To this was sprayed 210 g of 10% hydroxypropylcellulose solution to effect granulation. After drying, the thus obtained granules were passed through a 20 mesh screen, mixed with 2.1 g of magnesium stearate and then made into tablets of 100 mg per tablet by applying the resulting granules to a rotary tabletting machine (manufactured by Hata Tekkosyo) using a die/punch system of φ 6.5 mm×7.8 R. Using a coating apparatus (manufactured by Freund Sangyo), 350 g of a coating solution containing 20.3 g of hydroxypropylmethylcellulose, 2.8 g of polyethylene glycol 6000, 11.2 g of titanium oxide and 0.7 g of talc was sprayed on the thus prepared tablets, thereby obtaining film-coated tablets, each tablet having 5 mg of coating.

We claim:

1. An azole derivative represented by the following formula (I)

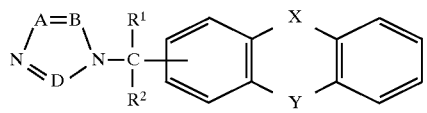 (I)

wherein $R^1$ and $R^2$ respectively represent a member selected from the group consisting of a hydrogen atom, a lower alkyl group and a phenyl group which may be substituted with a halogen atom, A, B, and D each represents a group of the formula

X represents a single bond, Y represents a group of the formula

wherein $R^3$ and $R^4$ each represents a hydrogen atom or a lower alkyl group; and a salt thereof, or a hydrate thereof.

2. The azole derivative or a salt thereof according to claim 1, wherein $R^1$ and $R^2$ are the same or different from each other and each represents a hydrogen atom or a lower alkyl group, X is a single bond and Y is a group represented by the formula

3. A pharmaceutical composition which comprises a therapeutically effective amount of the azole derivative of claim 1 or a pharmaceutically acceptable salt thereof as an active ingredient and a pharmaceutical carrier.

4. The azole derivative or a salt thereof according to claim 1, which is 2-[1-(1H-imidazol-1-yl)ethyl]carbazole.

5. The azole derivative or a salt thereof according to claim 1, which is (S)-(−)-2-[1-(1H-imidazol-1-yl)ethyl]carbazole.

6. The azole derivative or a salt thereof according to claim 1, wherein $R^1$–$R^4$ are hydrogen X is a single bond and Y is a group represented by the formula -$NR^4$.

7. A pharmaceutical composition which comprises a therapeutically effective amount of the azole derivative of claim 6 or a pharmaceutically acceptable salt thereof as an active ingredient and a pharmaceutically acceptable carrier.

* * * * *